(12) United States Patent
Shadduck et al.

(10) Patent No.: US 9,901,394 B2
(45) Date of Patent: Feb. 27, 2018

(54) MEDICAL ABLATION SYSTEM AND METHOD OF MAKING

(71) Applicant: Hermes Innovations LLC, Cupertino, CA (US)

(72) Inventors: John H. Shadduck, Menlo Park, CA (US); Benedek Orczy-Timko, Budapest (HU); Aaron Germain, San Jose, CA (US); Csaba Truckai, Saratoga, CA (US)

(73) Assignee: Hermes Innovations LLC, Cupertino, CA (US)

( * ) Notice: Subject to any disclaimer, the term of this patent is extended or adjusted under 35 U.S.C. 154(b) by 0 days.

(21) Appl. No.: 13/857,068

(22) Filed: Apr. 4, 2013

(65) Prior Publication Data

US 2014/0303611 A1   Oct. 9, 2014

(51) Int. Cl.
*A61B 18/14* (2006.01)
*A61B 18/00* (2006.01)

(52) U.S. Cl.
CPC .. *A61B 18/148* (2013.01); *A61B 2018/00202* (2013.01); *A61B 2018/00791* (2013.01); *A61B 2018/00875* (2013.01); *A61B 2018/1422* (2013.01); *A61B 2018/1475* (2013.01); *A61B 2218/002* (2013.01); *A61B 2218/007* (2013.01)

(58) Field of Classification Search
CPC ... A61B 18/14; A61B 18/148; A61B 18/1482; A61B 2018/1422; A61B 2018/00601; A61B 2018/00589; A61B 2018/00595; A61B 2018/1412; A61B 2018/1475; A61B 2018/00577

USPC ......................................................... 606/41
See application file for complete search history.

(56) References Cited

U.S. PATENT DOCUMENTS

| | | |
|---|---|---|
| 3,903,891 A | 9/1975 | Brayshaw |
| 4,428,748 A | 1/1984 | Peyman et al. |
| 4,949,718 A | 8/1990 | Neuwirth et al. |
| 4,979,948 A | 12/1990 | Geddes et al. |
| 5,045,056 A | 9/1991 | Behl |
| 5,078,717 A | 1/1992 | Parins |
| 5,084,044 A | 1/1992 | Quint |

(Continued)

FOREIGN PATENT DOCUMENTS

| | | |
|---|---|---|
| CN | 101198288 A | 6/2008 |
| EP | 1236440 A1 | 9/2002 |

(Continued)

OTHER PUBLICATIONS

U.S. Appl. No. 13/975,139, filed Aug. 23, 2013, Truckai et al.

(Continued)

*Primary Examiner* — Michael Peffley
(74) *Attorney, Agent, or Firm* — Wilson Sonsini Goodrich & Rosati

(57) ABSTRACT

An electrosurgical device comprises an elongated shaft having an axis with an interior channel extending along the axis to an opening in a distal end of the shaft. The channel is configured to be coupled to a negative pressure source, and an electrode with a conductive, usually hook-shaped, distal portion is coupled to the shaft and moveable between a first position in which a distal tip of the electrode is disposed proximate to a periphery of the opening of and a second position in which the distal electrode tip is exposed and spaced apart from the opening.

25 Claims, 7 Drawing Sheets

(56) References Cited

U.S. PATENT DOCUMENTS

| | | | |
|---|---|---|---|
| 5,191,883 A | 3/1993 | Lennox et al. | |
| 5,197,963 A * | 3/1993 | Parins | A61B 18/1482 606/41 |
| 5,242,390 A | 9/1993 | Goldrath | |
| 5,248,312 A | 9/1993 | Langberg | |
| 5,277,201 A | 1/1994 | Stern | |
| 5,282,799 A | 2/1994 | Rydell | |
| 5,324,254 A * | 6/1994 | Phillips | 604/21 |
| 5,344,435 A | 9/1994 | Turner et al. | |
| 5,374,261 A | 12/1994 | Yoon | |
| 5,401,272 A | 3/1995 | Perkins | |
| 5,401,274 A * | 3/1995 | Kusunoki | A61B 18/1482 606/41 |
| 5,429,136 A | 7/1995 | Milo et al. | |
| 5,441,498 A | 8/1995 | Perkins | |
| 5,443,470 A | 8/1995 | Stern et al. | |
| 5,456,689 A | 10/1995 | Kresch et al. | |
| 5,496,314 A * | 3/1996 | Eggers | 606/41 |
| 5,501,681 A | 3/1996 | Neuwirth et al. | |
| 5,505,730 A | 4/1996 | Edwards | |
| 5,507,725 A | 4/1996 | Savage et al. | |
| 5,558,672 A | 9/1996 | Edwards | |
| 5,562,703 A | 10/1996 | Desai | |
| 5,562,720 A | 10/1996 | Stern et al. | |
| 5,575,788 A | 11/1996 | Baker et al. | |
| 5,584,872 A | 12/1996 | LaFontaine et al. | |
| 5,622,647 A | 4/1997 | Kerr et al. | |
| 5,647,848 A | 7/1997 | Jorgensen | |
| 5,653,684 A | 8/1997 | Laptewicz et al. | |
| 5,653,692 A | 8/1997 | Masterson et al. | |
| 5,662,647 A * | 9/1997 | Crow | A61B 18/14 606/41 |
| 5,672,174 A * | 9/1997 | Gough | A61B 18/1477 606/41 |
| 5,681,308 A | 10/1997 | Edwards et al. | |
| 5,697,281 A | 12/1997 | Eggers | |
| 5,697,882 A | 12/1997 | Eggers | |
| 5,713,942 A | 2/1998 | Stern et al. | |
| 5,733,298 A | 3/1998 | Berman et al. | |
| 5,769,846 A | 6/1998 | Edwards et al. | |
| 5,769,880 A | 6/1998 | Truckai et al. | |
| 5,779,662 A | 7/1998 | Berman | |
| 5,800,493 A | 9/1998 | Stevens et al. | |
| 5,810,802 A | 9/1998 | Panescu et al. | |
| 5,827,273 A | 10/1998 | Edwards | |
| 5,843,020 A | 12/1998 | Tu et al. | |
| 5,846,239 A | 12/1998 | Swanson et al. | |
| 5,860,974 A | 1/1999 | Abele | |
| 5,876,340 A | 3/1999 | Tu et al. | |
| 5,879,347 A | 3/1999 | Saadat | |
| 5,891,094 A | 4/1999 | Masterson et al. | |
| 5,891,134 A | 4/1999 | Goble et al. | |
| 5,891,136 A | 4/1999 | McGee | |
| 5,902,251 A | 5/1999 | vanHooydonk | |
| 5,904,651 A | 5/1999 | Swanson et al. | |
| 5,925,038 A | 7/1999 | Panescu et al. | |
| 5,954,714 A | 9/1999 | Saadat et al. | |
| 5,964,755 A | 10/1999 | Edwards | |
| 5,976,129 A | 11/1999 | Desai | |
| 5,980,515 A | 11/1999 | Tu | |
| 5,997,534 A | 12/1999 | Tu et al. | |
| 6,024,743 A | 2/2000 | Edwards | |
| 6,026,331 A | 2/2000 | Feldberg et al. | |
| 6,041,260 A | 3/2000 | Stern et al. | |
| 6,053,909 A | 4/2000 | Shadduck | |
| 6,057,689 A | 5/2000 | Saadat | |
| 6,086,581 A | 7/2000 | Reynolds et al. | |
| 6,113,597 A | 9/2000 | Eggers | |
| 6,139,570 A | 10/2000 | Saadat et al. | |
| 6,146,378 A | 11/2000 | Mikus et al. | |
| 6,149,620 A | 11/2000 | Baker et al. | |
| 6,214,003 B1 | 4/2001 | Morgan et al. | |
| 6,228,078 B1 | 5/2001 | Eggers et al. | |
| 6,254,599 B1 | 7/2001 | Lesh et al. | |
| 6,283,962 B1 | 9/2001 | Tu et al. | |
| 6,296,639 B1 | 10/2001 | Truckai et al. | |
| 6,302,904 B1 | 10/2001 | Wallsten et al. | |
| 6,315,776 B1 | 11/2001 | Edwards et al. | |
| 6,366,818 B1 | 4/2002 | Bolmsjo | |
| 6,387,088 B1 | 5/2002 | Shattuck et al. | |
| 6,395,012 B1 | 5/2002 | Yoon et al. | |
| 6,409,722 B1 | 6/2002 | Hoey et al. | |
| 6,416,508 B1 | 7/2002 | Eggers et al. | |
| 6,416,511 B1 | 7/2002 | Lesh et al. | |
| 6,443,947 B1 | 9/2002 | Marko et al. | |
| 6,491,690 B1 | 12/2002 | Goble et al. | |
| 6,508,815 B1 | 1/2003 | Strul et al. | |
| 6,551,310 B1 | 4/2003 | Ganz et al. | |
| 6,565,561 B1 | 5/2003 | Goble et al. | |
| 6,589,237 B2 | 7/2003 | Woloszko et al. | |
| 6,602,248 B1 | 8/2003 | Sharps et al. | |
| 6,607,545 B2 | 8/2003 | Kammerer et al. | |
| 6,622,731 B2 * | 9/2003 | Daniel et al. | 128/898 |
| 6,635,054 B2 | 10/2003 | Fjield et al. | |
| 6,635,055 B1 | 10/2003 | Cronin | |
| 6,663,626 B2 | 12/2003 | Truckai et al. | |
| 6,673,071 B2 | 1/2004 | Van Dusseldorp et al. | |
| 6,699,241 B2 | 3/2004 | Rappaport et al. | |
| 6,726,684 B1 | 4/2004 | Woloszko et al. | |
| 6,736,811 B2 | 5/2004 | Panescu et al. | |
| 6,746,447 B2 | 6/2004 | Davison et al. | |
| 6,758,847 B2 | 7/2004 | Maguire | |
| 6,780,178 B2 | 8/2004 | Palanker et al. | |
| 6,802,839 B2 | 10/2004 | Behl | |
| 6,813,520 B2 | 11/2004 | Truckai et al. | |
| 6,814,730 B2 | 11/2004 | Li | |
| 6,832,996 B2 | 12/2004 | Woloszko et al. | |
| 6,837,887 B2 | 1/2005 | Woloszko et al. | |
| 6,837,888 B2 | 1/2005 | Ciarrocca et al. | |
| 6,840,935 B2 | 1/2005 | Lee | |
| 6,872,205 B2 | 3/2005 | Lesh et al. | |
| 6,896,674 B1 | 5/2005 | Woloszko et al. | |
| 6,905,497 B2 | 6/2005 | Truckai et al. | |
| 6,923,805 B1 | 8/2005 | LaFontaine et al. | |
| 6,929,642 B2 | 8/2005 | Xiao et al. | |
| 6,949,096 B2 | 9/2005 | Davison et al. | |
| 6,951,569 B2 | 10/2005 | Nohilly et al. | |
| 6,954,977 B2 | 10/2005 | Maguire et al. | |
| 6,960,203 B2 | 11/2005 | Xiao et al. | |
| 7,074,217 B2 | 7/2006 | Strul et al. | |
| 7,083,614 B2 | 8/2006 | Fijield et al. | |
| 7,087,052 B2 | 8/2006 | Sampson et al. | |
| 7,108,696 B2 * | 9/2006 | Daniel et al. | 606/41 |
| 7,118,590 B1 | 10/2006 | Cronin | |
| 7,150,747 B1 | 12/2006 | McDonald et al. | |
| 7,175,734 B2 | 2/2007 | Stewart et al. | |
| 7,179,255 B2 | 2/2007 | Lettice et al. | |
| 7,186,234 B2 | 3/2007 | Dahla et al. | |
| 7,192,430 B2 | 3/2007 | Truckai et al. | |
| 7,238,185 B2 | 7/2007 | Palanker et al. | |
| 7,270,658 B2 | 9/2007 | Woloszko et al. | |
| 7,276,063 B2 | 10/2007 | Davison et al. | |
| 7,278,994 B2 * | 10/2007 | Goble | 606/48 |
| 7,294,126 B2 | 11/2007 | Sampson et al. | |
| 7,297,143 B2 | 11/2007 | Woloszko et al. | |
| 7,326,201 B2 | 2/2008 | Fijield et al. | |
| 7,331,957 B2 | 2/2008 | Woloszko et al. | |
| RE40,156 E | 3/2008 | Sharps et al. | |
| 7,371,231 B2 | 5/2008 | Rioux et al. | |
| 7,371,235 B2 | 5/2008 | Thompson et al. | |
| 7,381,208 B2 | 6/2008 | van der Walt et al. | |
| 7,387,628 B1 | 6/2008 | Behl et al. | |
| 7,407,502 B2 | 8/2008 | Strul et al. | |
| 7,419,500 B2 | 9/2008 | Marko et al. | |
| 7,452,358 B2 | 11/2008 | Stern et al. | |
| 7,462,178 B2 | 12/2008 | Woloszko et al. | |
| 7,500,973 B2 | 3/2009 | Vancelette et al. | |
| 7,512,445 B2 | 3/2009 | Truckai et al. | |
| 7,530,979 B2 | 5/2009 | Ganz et al. | |
| 7,549,987 B2 | 6/2009 | Shadduck | |
| 7,556,628 B2 | 7/2009 | Utley et al. | |
| 7,566,333 B2 | 7/2009 | Van Wyk et al. | |
| 7,572,251 B1 | 8/2009 | Davison et al. | |
| 7,604,633 B2 | 10/2009 | Truckai et al. | |

(56) References Cited

U.S. PATENT DOCUMENTS

| | | | |
|---|---|---|---|
| 7,625,368 B2 | 12/2009 | Schechter et al. | |
| 7,674,259 B2 | 3/2010 | Shadduck | |
| 7,678,106 B2 | 3/2010 | Lett | |
| 7,708,733 B2 | 5/2010 | Sanders et al. | |
| 7,717,909 B2 | 5/2010 | Strul et al. | |
| 7,736,362 B2 | 6/2010 | Eberl et al. | |
| 7,749,159 B2 | 7/2010 | Crowley et al. | |
| 7,824,398 B2 * | 11/2010 | Woloszko | A61B 18/1402 606/32 |
| 7,824,405 B2 | 11/2010 | Woloszko et al. | |
| 7,846,160 B2 | 12/2010 | Payne et al. | |
| 7,879,034 B2 | 2/2011 | Woloszko et al. | |
| 7,918,795 B2 | 4/2011 | Grossman | |
| 7,985,188 B2 | 7/2011 | Felts et al. | |
| 8,197,476 B2 | 6/2012 | Truckai | |
| 8,197,477 B2 | 6/2012 | Truckai | |
| 8,372,068 B2 | 2/2013 | Truckai | |
| 8,382,753 B2 | 2/2013 | Truckai | |
| 8,486,096 B2 | 7/2013 | Robertson et al. | |
| 8,540,708 B2 | 9/2013 | Truckai et al. | |
| 8,690,873 B2 | 4/2014 | Truckai et al. | |
| 8,998,901 B2 | 4/2015 | Truckai et al. | |
| 2002/0022870 A1 | 2/2002 | Truckai et al. | |
| 2002/0058933 A1 | 5/2002 | Christopherson et al. | |
| 2002/0068934 A1 | 6/2002 | Edwards et al. | |
| 2002/0082635 A1 | 6/2002 | Kammerer et al. | |
| 2002/0183742 A1 | 12/2002 | Carmel et al. | |
| 2003/0065321 A1 | 4/2003 | Carmel et al. | |
| 2003/0130655 A1 | 7/2003 | Woloszko et al. | |
| 2003/0153905 A1 | 8/2003 | Edwards et al. | |
| 2003/0171743 A1 | 9/2003 | Tasto et al. | |
| 2003/0176816 A1 * | 9/2003 | Maguire et al. | 601/2 |
| 2003/0208200 A1 | 11/2003 | Palanker et al. | |
| 2003/0216725 A1 | 11/2003 | Woloszko et al. | |
| 2004/0002702 A1 | 1/2004 | Xiao et al. | |
| 2004/0010249 A1 | 1/2004 | Truckai et al. | |
| 2004/0087936 A1 | 5/2004 | Stern et al. | |
| 2004/0102770 A1 | 5/2004 | Goble | |
| 2004/0215180 A1 | 10/2004 | Starkebaum et al. | |
| 2004/0215182 A1 | 10/2004 | Lee | |
| 2004/0215296 A1 | 10/2004 | Ganz et al. | |
| 2004/0230190 A1 | 11/2004 | Dahla et al. | |
| 2005/0075630 A1 | 4/2005 | Truckai et al. | |
| 2005/0165389 A1 | 7/2005 | Swain et al. | |
| 2005/0182397 A1 | 8/2005 | Ryan | |
| 2005/0192652 A1 | 9/2005 | Cioanta et al. | |
| 2005/0228372 A1 | 10/2005 | Truckai et al. | |
| 2005/0240176 A1 | 10/2005 | Oral et al. | |
| 2005/0251131 A1 | 11/2005 | Lesh | |
| 2006/0009756 A1 | 1/2006 | Francischelli et al. | |
| 2006/0052771 A1 | 3/2006 | Sartor et al. | |
| 2006/0084969 A1 | 4/2006 | Truckai et al. | |
| 2006/0089637 A1 | 4/2006 | Werneth et al. | |
| 2006/0178670 A1 | 8/2006 | Woloszko et al. | |
| 2006/0189972 A1 | 8/2006 | Tasto et al. | |
| 2006/0189976 A1 | 8/2006 | Karni et al. | |
| 2006/0224154 A1 | 10/2006 | Shadduck et al. | |
| 2006/0259025 A1 | 11/2006 | Dahla | |
| 2007/0021743 A1 | 1/2007 | Rioux et al. | |
| 2007/0083192 A1 | 4/2007 | Welch | |
| 2007/0161981 A1 | 7/2007 | Sanders et al. | |
| 2007/0213704 A1 | 9/2007 | Truckai et al. | |
| 2007/0288075 A1 | 11/2007 | Dowlatshahi | |
| 2007/0282323 A1 | 12/2007 | Wolozko et al. | |
| 2007/0287996 A1 | 12/2007 | Rioux | |
| 2007/0293853 A1 | 12/2007 | Truckai et al. | |
| 2008/0058797 A1 | 3/2008 | Rioux | |
| 2008/0097242 A1 | 4/2008 | Cai | |
| 2008/0097425 A1 | 4/2008 | Truckai | |
| 2008/0125765 A1 | 5/2008 | Berenshteyn et al. | |
| 2008/0125770 A1 | 5/2008 | Kleyman | |
| 2008/0154238 A1 | 6/2008 | McGuckin | |
| 2008/0183132 A1 | 7/2008 | Davies et al. | |
| 2008/0208189 A1 | 8/2008 | Van Wyk et al. | |
| 2008/0221567 A1 | 9/2008 | Sixto, Jr. | |
| 2008/0249518 A1 | 10/2008 | Warnking et al. | |
| 2008/0281317 A1 | 11/2008 | Gobel | |
| 2009/0048593 A1 | 2/2009 | Ganz et al. | |
| 2009/0054888 A1 | 2/2009 | Cronin | |
| 2009/0054892 A1 | 2/2009 | Rioux et al. | |
| 2009/0076494 A1 | 3/2009 | Azure | |
| 2009/0105703 A1 | 4/2009 | Shadduck | |
| 2009/0131927 A1 | 5/2009 | Kastelein et al. | |
| 2009/0149846 A1 | 6/2009 | Hoey et al. | |
| 2009/0163908 A1 | 6/2009 | MacLean et al. | |
| 2009/0209956 A1 | 8/2009 | Marion | |
| 2009/0306654 A1 | 12/2009 | Garbagnati | |
| 2010/0004595 A1 | 1/2010 | Nguyen et al. | |
| 2010/0036372 A1 | 2/2010 | Truckai et al. | |
| 2010/0042095 A1 | 2/2010 | Bigley et al. | |
| 2010/0042097 A1 | 2/2010 | Newton et al. | |
| 2010/0049190 A1 | 2/2010 | Long et al. | |
| 2010/0106152 A1 | 4/2010 | Truckai et al. | |
| 2010/0114089 A1 | 5/2010 | Truckai et al. | |
| 2010/0121319 A1 | 5/2010 | Chu et al. | |
| 2010/0125269 A1 | 5/2010 | Emmons et al. | |
| 2010/0137855 A1 | 6/2010 | Berjano Zanon et al. | |
| 2010/0137857 A1 | 6/2010 | Shiroff et al. | |
| 2010/0152725 A1 | 6/2010 | Pearson et al. | |
| 2010/0185191 A1 | 7/2010 | Carr et al. | |
| 2010/0198214 A1 | 8/2010 | Layton et al. | |
| 2010/0204688 A1 | 8/2010 | Hoey et al. | |
| 2010/0217256 A1 | 8/2010 | Strul et al. | |
| 2010/0228239 A1 | 9/2010 | Freed | |
| 2010/0228245 A1 | 9/2010 | Sampson et al. | |
| 2010/0286680 A1 | 11/2010 | Kleyman | |
| 2011/0004205 A1 | 1/2011 | Chu et al. | |
| 2011/0060391 A1 | 3/2011 | Unetich et al. | |
| 2011/0112524 A1 | 5/2011 | Stern et al. | |
| 2011/0196401 A1 | 8/2011 | Robertson et al. | |
| 2011/0282340 A1 | 11/2011 | Toth et al. | |
| 2012/0116384 A1 | 5/2012 | Truckai | |
| 2012/0130361 A1 | 5/2012 | Toth et al. | |
| 2012/0330292 A1 | 12/2012 | Shadduck et al. | |
| 2013/0172870 A1 | 7/2013 | Germain et al. | |
| 2013/0267937 A1 | 10/2013 | Shadduck et al. | |
| 2013/0296847 A1 | 11/2013 | Germain et al. | |
| 2013/0331833 A1 | 12/2013 | Bloom | |
| 2013/0345705 A1 | 12/2013 | Truckai et al. | |
| 2014/0336632 A1 | 11/2014 | Toth et al. | |
| 2015/0105791 A1 | 4/2015 | Truckai | |
| 2015/0119916 A1 | 4/2015 | Dietz et al. | |
| 2015/0173827 A1 | 6/2015 | Bloom et al. | |
| 2015/0182281 A1 | 7/2015 | Truckai et al. | |
| 2016/0095615 A1 | 4/2016 | Orczy-Timko et al. | |
| 2017/0215912 A1 | 8/2017 | Truckai | |
| 2017/0231681 A1 | 8/2017 | Toth et al. | |

FOREIGN PATENT DOCUMENTS

| | | |
|---|---|---|
| EP | 1595507 A2 | 11/2005 |
| EP | 2349044 A1 | 8/2011 |
| EP | 2493407 A1 | 9/2012 |
| EP | 2981222 A1 | 2/2016 |
| WO | WO 00/53112 A2 | 9/2000 |
| WO | WO 2005/122938 A1 | 12/2005 |
| WO | WO 2006/001455 A1 | 1/2006 |
| WO | WO2008/083407 A1 | 7/2008 |
| WO | WO-2010048007 A1 | 4/2010 |
| WO | WO 2011/053599 A1 | 5/2011 |
| WO | WO-2011060301 A1 | 5/2011 |
| WO | WO 2014/165715 A1 | 10/2014 |

OTHER PUBLICATIONS

Office action dated Nov. 6, 2013 for U.S. Appl. No. 13/938,032.
Office action dated Apr. 24, 2014 for U.S. Appl. No. 13/974,139.
European search report and search opinion dated Apr. 16, 2013 for EP Application No. 09822443.
European search report and search opinion dated Jul. 10, 2013 for EP Application No. 10827399.
International search report and written opinion dated Feb. 2, 2011 for PCT/US2010/056591.

(56) References Cited

OTHER PUBLICATIONS

International search report and written opinion dated Dec. 10, 2009 for PCT/US2009/060703.
International search report and written opinion dated Dec. 14, 2010 for PCT/US2010/054150.
Office action dated Mar. 12, 2012 for U.S. Appl. No. 12/541,043.
Office action dated Mar. 12, 2012 for U.S. Appl. No. 12/541,050.
Office action dated Sep. 28, 2012 for U.S. Appl. No. 12/541,043.
Office action dated Sep. 28, 2012 for U.S. Appl. No. 12/541,050.
Office action dated Sep. 28, 2012 for U.S. Appl. No. 12/605,929.
Office action dated Dec. 6, 2011 for U.S. Appl. No. 13/281,846.
Office action dated Dec. 22, 2011 for U.S. Appl. No. 13/281,856.
U.S. Appl. No. 13/938,032, filed Jul. 9, 2013, Truckai et al.
U.S. Appl. No. 14/341,121, filed Jul. 25, 2014, Toth et al.
U.S. Appl. No. 14/508,856, filed Oct. 7, 2014, Truckai.
Notice of allowance dated Jan. 9, 2014 for U.S. Appl. No. 13/938,032.
Notice of allowance dated Mar. 5, 2012 for U.S. Appl. No. 13/281,846.
Notice of allowance dated Mar. 5, 2012 for U.S. Appl. No. 13/281,856.
Notice of allowance dated Mar. 29, 2013 for U.S. Appl. No. 12/605,546.
Notice of allowance dated May 9, 2014 for U.S. Appl. No. 12/944,466.
Notice of allowance dated May 24, 2013 for U.S. Appl. No. 12/605,929.
Notice of allowance dated Nov. 15, 2012 for U.S. Appl. No. 12/541,043.
Notice of allowance dated Nov. 15, 2012 for U.S. Appl. No. 12/541,050.
Notice of allowance dated Dec. 2, 2014 for U.S. Appl. No. 13/975,139.
International Search Report dated Sep. 10, 2014 for PCT/US2014/032895.
Office action dated Jan. 28, 2013 for U.S. Appl. No. 12/605,546.
Office action dated Jun. 18, 2012 for U.S. Appl. No. 12/605,546.
Office action dated Sep. 22, 2014 for U.S. Appl. No. 13/281,805.
Office action dated Dec. 4, 2014 for U.S. Appl. No. 13/236,471.
Office action dated Dec. 16, 2014 for U.S. Appl. No. 13/281,805.
Co-pending U.S. Appl. No. 14/657,684, filed Mar. 13, 2015.
Co-pending U.S. Appl. No. 14/864,379, filed Sep. 24, 2015.
Office action dated Sep. 24, 2015 for U.S. Appl. No. 13/236,471.
Notice of allowance dated Feb. 25, 2015 for U.S. Appl. No. 13/975,139.
Office action dated May 22, 2015 for U.S. Appl. No. 14/657,684.
Office action dated Jul. 23, 2015 for U.S. Appl. No. 13/281,805.
Co-pending U.S. Appl. No. 15/008,341, filed Jan. 27, 2016.
International Search Report dated Jul. 6, 2016 for PCT/US16/25509.
Notice of Allowance dated Jan. 27, 2017 for U.S. Appl. No. 13/236,471.
Notice of Allowance dated Jan. 27, 2017 for U.S. Appl. No. 14/508,856.
Office Action dated Mar. 9, 2017 for U.S. Appl. No. 15/091,402.
Office Action dated Sep. 30, 2016 for U.S. Appl. No. 15/091,402.
Notice of Allowance dated Aug. 2, 2016 for U.S. Appl. No. 13/281,805.
Office Action dated Mar. 31, 2016 for U.S. Appl. No. 13/281,805.
Office Action dated Apr. 22, 2016 for U.S. Appl. No. 14/657,684.
Office Action dated Jun. 29, 2016 for U.S. Appl. No. 14/508,856.
Office Action dated Jul. 5, 2016 for U.S. Appl. No. 13/236,471.
Office Action dated Nov. 2, 2016 for U.S. Appl. No. 14/657,684.
Office Action dated Mar. 14, 2017 for U.S. Appl. No. 15/410,723.
Office Action dated Apr. 18, 2017 for U.S. Appl. No. 14/657,684.

\* cited by examiner

MEDICAL ABLATION SYSTEM AND METHOD OF MAKING

FIELD OF THE INVENTION

This invention relates to medical instruments and systems for applying energy to tissue, and more particularly relates to an electrosurgical probe adapted for ablating, cutting and treating tissue in an endoscopic procedure.

BACKGROUND OF THE INVENTION

Various types of medical instruments utilizing radiofrequency (RF) energy, laser energy and the like have been developed for delivering thermal energy to tissue, for example to ablate tissue and to cut tissue. Arthroscopic and other endoscopic electrosurgical tools often comprise treatment electrodes of different configurations where the tools may optionally be combined with irrigation and/or aspiration tools for performing particular minimally invasive procedures. Often the nature of the electrode limits use of a particular tool, and tools must be exchanged during a procedure to perform different tasks. For these reasons, it would be desirable to provide new and different designs for electrosurgical tools that allow the tools to be re-configured during a procedure to perform different tasks. At least some of these objectives will be met by the inventions described below.

SUMMARY OF THE INVENTION

In a first aspect of the present invention, an electrosurgical device comprises an elongated shaft having an axis with an interior channel extending along the axis to an opening in a distal end of the shaft. The channel is configured to be coupled to a negative pressure source, and an electrode with a hook-shaped distal portion is coupled to the shaft and moveable between a first position in which a distal tip of the electrode is disposed at a periphery of the opening and a second position in which the distal tip extends distally beyond the opening. With the distal portion of the electrode in the first position, the tool is particularly useful for surface ablation of tissue such as cartilage. With the distal portion of the electrode in the second position, the tool is particularly useful for cutting tissue structures. In one application, the hook-shaped electrode can be used in a lateral release, which is an arthroscopic procedure for releasing tight capsular structures, e.g., the lateral retinaculum, on the outer or lateral aspect of the kneecap. Such a procedure is performed due to pain related to the kneecap being pulled over to the outer (lateral) side and not being able to move properly in a groove of the femur bone as the knee bends and straightens. In a second aspect of the present invention, an electrosurgical device comprises an elongated shaft extending along an axis with an interior channel extending to an opening with a periphery in a working end. The channel is adapted to be coupled to a negative pressure source. A moveable electrode having a conductive portion with a proximal end and a distal end is coupled to the shaft so that the distal end of the conductive portion is located proximate the periphery of the opening when the electrode is in a proximally retracted position and the distal end of the electrode extends distally beyond the periphery when the electrode is in a distally extended position. With the conductive portion of the electrode in the first position, the tool is particularly useful for surface ablation of tissue and cautery. With the conductive portion of the electrode in the second position, the tool is particularly useful for capturing and cutting tissue structures.

Usually, in both aspects, the electrode of the electrosurgical device is mounted to axially translate between the first and second positions. Optionally, the electrode is mounted to rotate about the axis between the first and second positions. In another variation, the electrode of the electrosurgical device of is mounted to axially translate and/or rotate about the axis between the first and second positions.

In specific embodiments, the electrosurgical device may further comprise a valve in the interior channel for controlling fluid flow therethrough. An exterior of the electrosurgical shaft may comprise a second electrode. The electrosurgical device may further comprise a rotator coupled to the electrode, where the rotator causes the electrode to rotate as it is being axially translated. The opening of the electrosurgical device may define a plane which is angled relative to the axis of the shaft, and the hook-shaped portion of the electrode may be turned so that a back of the hook portion extends outwardly above the plane when the electrode is in the first position. The electrosurgical device may still further comprise a temperature sensor and/or impedance sensing electrodes near a distal end of the shaft. Alternatively, or in addition to the sensors, the electrosurgical device may further comprise a temperature-responsive current limiting element in series with the electrode in order to inhibit or prevent overheating of distention fluid in a treatment site.

DETAILED DESCRIPTION OF THE INVENTION

Figure 1A:
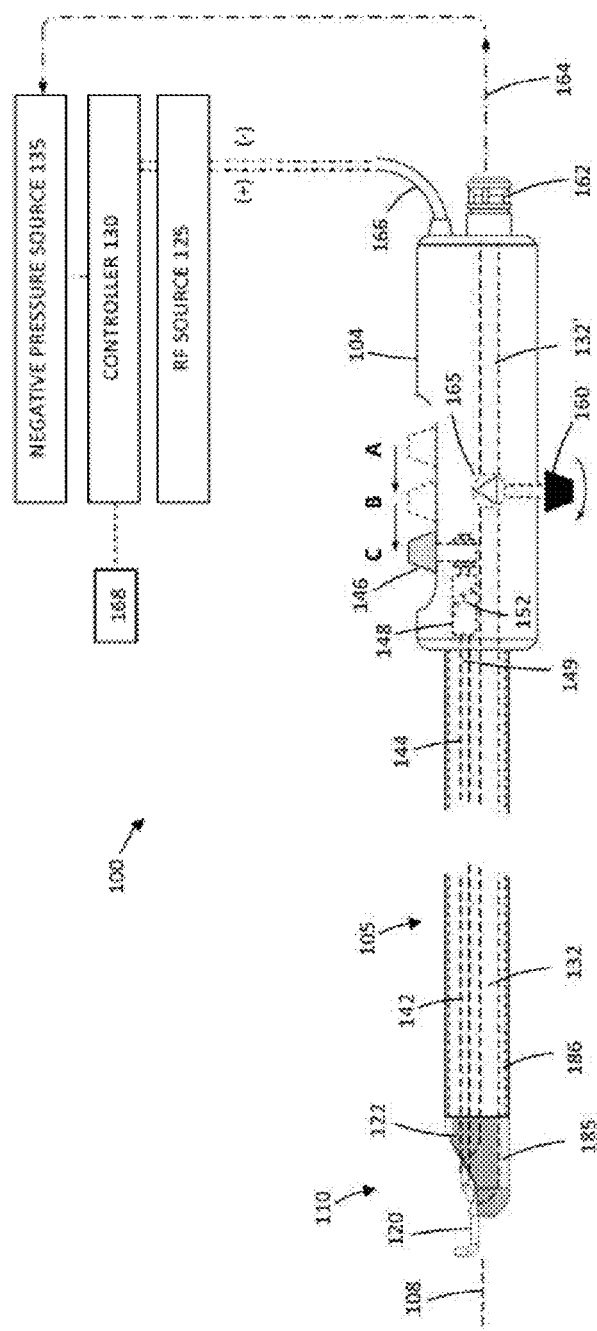
FIG. 1A is side view of an electrosurgical probe corresponding to the invention that includes an elongated shaft extending along an axis to a working end with a re-configurable electrode.
Figure 1B:
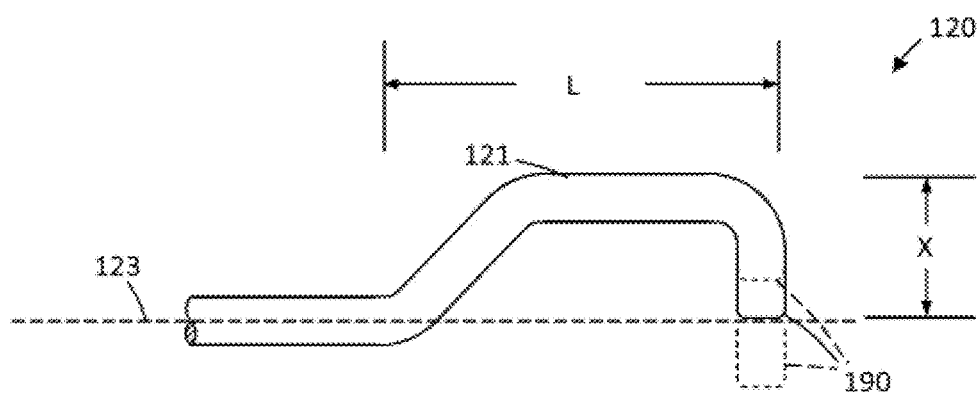
FIGS. 1B and 1C illustrate various embodiments of the re-configurable electrode of FIG. 1.
Figure 1C:
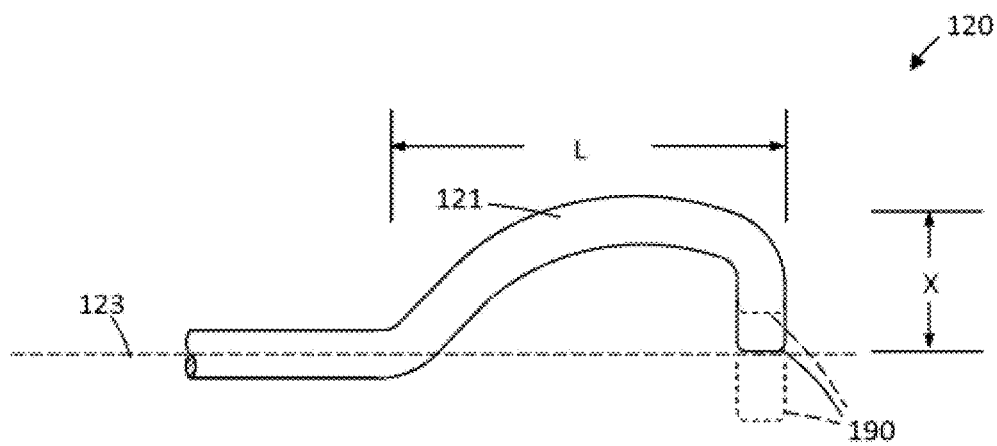
Figure 2A:
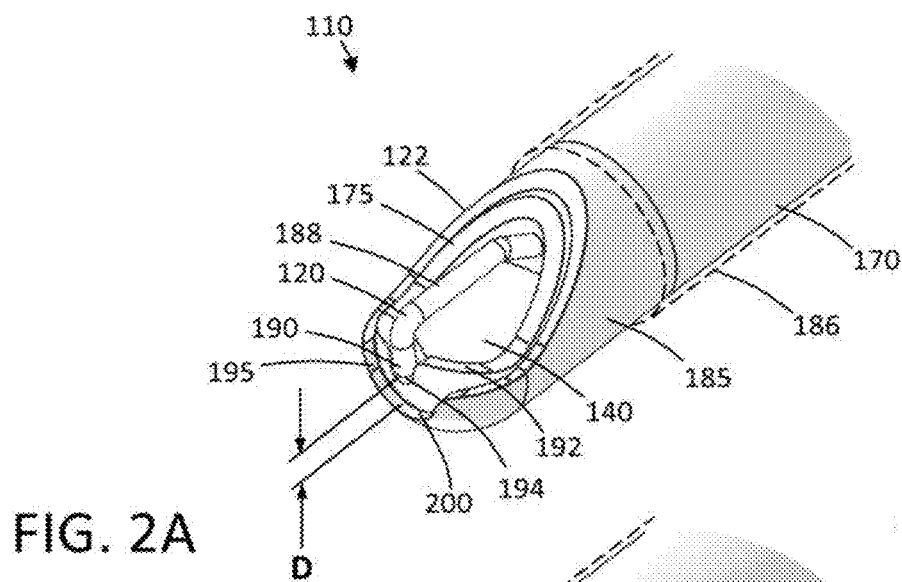
FIG. 2A is a perspective view of the working end of FIG. 1 with the moveable electrode in a first position.

Referring now to the drawings and the reference numbers marked thereon, FIGS. 1A and 2A-2C illustrate one embodiment of electrosurgical probe 100 that includes handle portion 104 and elongated shaft 105 that extends about longitudinal axis 108. FIG. 1 is a schematic view of the probe in which the shaft 105 consists of an assembly further described below having a diameter ranging from about 3.0 mm to 6.0 mm and any suitable length for arthroscopy or another endoscopic procedure. The working end 110 carries an electrode arrangement including a moveable first polarity or active electrode 120 and a second polarity or return electrode 122 operatively coupled to an RF source 125 and controller 130. As can be seen in FIG. 1A, the shaft 105 has a fluid extraction channel 132 in communication with a negative pressure source 135 that can be a wall suction source in an operating room or a pump system in controller 130. In FIG. 2A, it can be seen that fluid channel 132 extends distally to an opening 140 in the working end 110 which is proximate the electrode 120.

In one embodiment in FIGS. 1A and 2A-2C, the first polarity electrode 120 has an elongated medial portion 142 that extends through a passageway 144 (or channel 132) in shaft 105 to an acutator mechanism 146 in the handle 104. The electrode 120 terminates in an electrically conductive portion free from insulation, with the conductive portion typically being hook-shaped as described in more detail below. In FIG. 1A, it can be seen that actuator 146 is adapted to slide from position A to position B to position C to thereby move the electrode 120 from the non-extended position of FIG. 2A to the extended position of FIG. 2B and then to the extended and rotated position of FIG. 2C. Any suitable actuator mechanism known in the art can be used to move the electrode 120 axially and rotationally, and in one variation shown in FIG. 1, a barrel 148 with a spiral groove 152 therein can translate linear motion of the actuator mechanism 146 to rotational motion. In another embodiment, the actuator 146 can be fixed to the proximal end 149 of electrode 120 and adapted to move both axially and rotationally to move the electrode 120 between the various positions shown in FIGS. 2A-2C. The moveable actuator 146 can be configured with detents that engages a portion of handle 104 to releaseably maintain the electrode 120 in one of the selected positions of FIGS. 2A-2C.

Referring again to FIG. 1A, a second actuator 160 in handle 104 is adapted to modulate outflows in fluid extraction channel 132. FIG. 1A shows the extraction channel portion 132' in handle 104 extends to a quick-connect 162 on a handle 104 to which an outflow tubing 164 is coupled that extends to the negative pressure source 135. The actuator 160 can operate any type of suitable valve 165 to control the amount of outflow from a treatment site, such as a knee or shoulder. In such an arthroscopic procedure, the fluid inflows are provided through an independent inflow path which can be through a fluid channel in an endoscope or through another independent cannula accessing the treatment site.

Still referring to FIG. 1A, an electrical cable 166 extends from RF source 125 and controller 130 to the handle 104 with leads in the handle coupled to the first and second electrodes. The system can include a footswitch 168 operatively connected to controller 130 for ON-OFF actuation of RF energy to the electrode arrangement. In another variation, the switch for actuation of RF energy can be positioned in the probe handle 104. The RF source and controller can provide for various power setting as is known in the art, and can use any radiofrequency known in the art for creating a plasma about the electrode 120 for cutting tissue.

Referring to FIGS. 1B and 1C, the active electrode 120 which includes the conductive portion of the electrode extending distally from the medial portion 142 is typically hook-shaped and may have an a square or trapezoidal profile, as shown in FIG. 1B, or may have a curved or arcuate profile, as shown in FIG. 1C. The hook portion will typically have a length L in the range from 3 mm to 10 mm and a depth X in the range from 2 mm to 6 mm. The hook-shaped active electrode will also include a back or a spine region 121 that remains exposed over a plane defined by the opening 140 when the electrode is proximally retracted and a distal tip 190 of the electrode engages or lies proximate to the periphery or perimeter 192 surrounding the opening 140. The distal tip 190 may terminate at, above, or below a centerline 123 of the electrode, as shown in full line and broken lines in FIGS. 1B and 1C.

Figure 3:
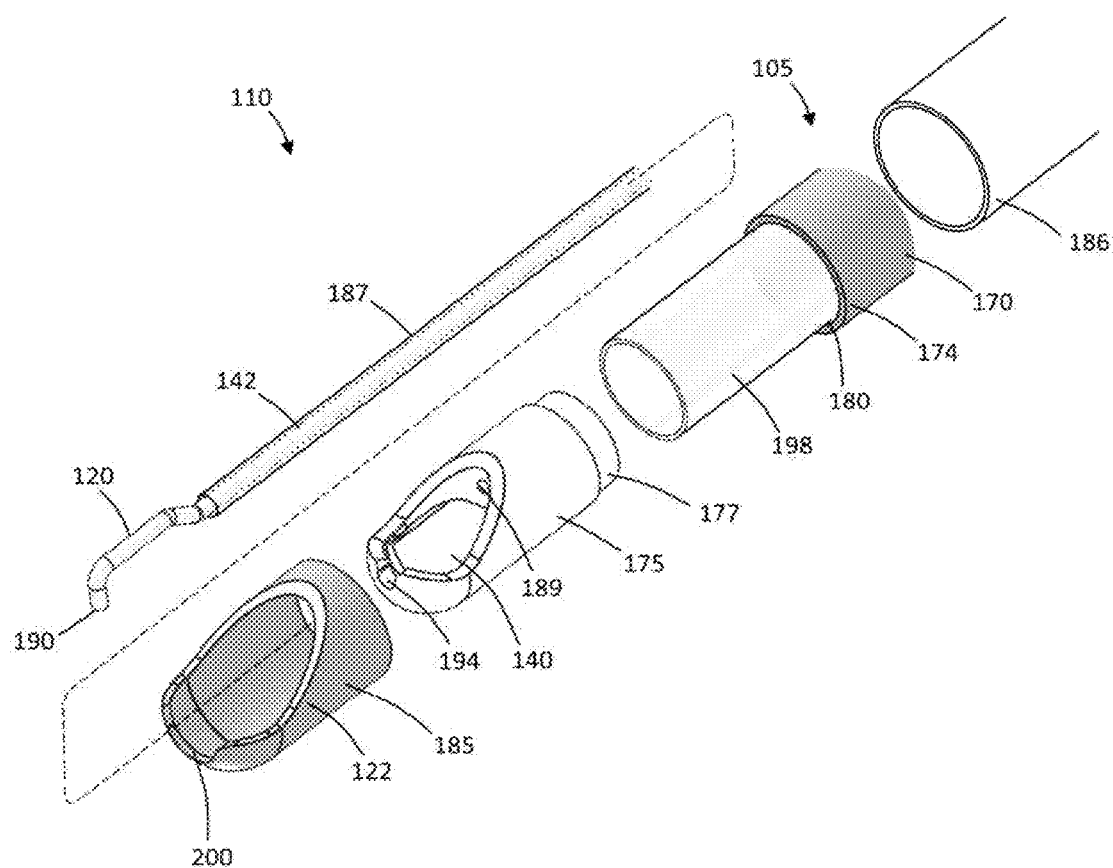
FIG. 3 is an exploded view of the components of the working end of FIG. 1.

The exploded view of a portion of the probe of FIG. 3 illustrates the components and assembly of the working end 110. In one variation shown in FIG. 3, the shaft 105 includes an elongate metal sleeve 170 (e.g., stainless steel) that is coupled to handle 104 which provides structural strength to the shaft 105 and further serves an electrical conductor to function as, or connect to, the return electrode 122. The proximal end of sleeve 170 is fixed to handle 104 with an electrical connector (not shown) within the handle coupling the sleeve 170 to cable 166 and a pole of the RF source 125 (see FIG. 1).

In FIG. 3, it can be seen that the distal end 174 of sleeve 170 couples with non-conductive ceramic body 175, which can be zirconium oxide, aluminum oxide or a similar material. In one variation, a reduced diameter proximal end 177 of ceramic body 175 can mate with bore 180 in sleeve 170. FIG. 3 further shows a metal distal body or housing 185 that is configured to slide over ceramic body 175 and then is welded to the distal end 174 of sleeve 170 to thus provide the assembled working end of FIG. 2A-2C. The metal distal body or housing 185 then functions as second polarity electrode 122 as can be understood from FIG. 2A-2C. In one variation, a thin-wall dielectric material 186 such a heat shrink material (PFA, FEP or the like) covers the sleeve 170 proximally from the distal metal housing 185 to the handle 104.

Figure 2B:
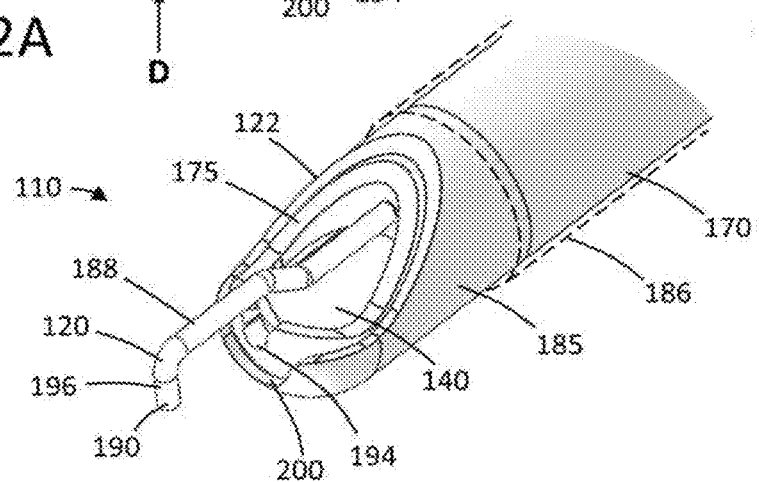
FIG. 2B is a perspective view of the working end of FIG. 1 with the moveable electrode in a second position.
Figure 2C:
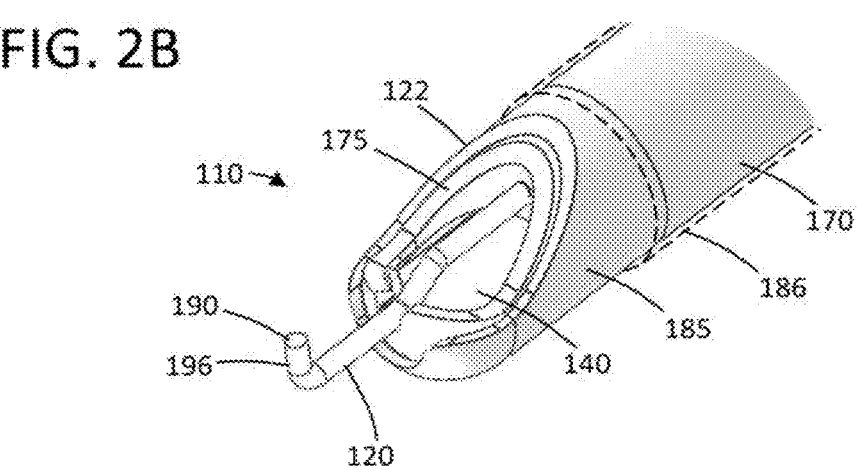
FIG. 2C is a perspective view of the working end of FIG. 1 with the moveable electrode in a third position.

In FIG. 3, it can be seen that first polarity electrode 120 and more particularly its medial portion 142 extends through a bore 189 in ceramic body 175. The elongated portion of electrode 120 is covered by a heat-shrink insulator 187 of a material such as FEP or PFA. The distal portion of electrode 120 is configured with bends or curvature to provide a hook-shaped electrode with an outermost electrode surface 188 that is approximately within an envelope defined by the cylindrical periphery of shaft 105 in the position of FIG. 2A. This configuration permits the physician to paint the outermost surface 188 of electrode 120 across a tissue surface to perform an electrosurgical surface ablation of such tissue. Referring to FIGS. 2A and 3, the distal tip 190 of electrode 120 in the position shown in FIG. 2A is configured to be disposed within or adjacent a periphery or perimeter 192 of opening 140 in the working end. More particularly, distal tip 190 in the position of FIG. 2A is configured to rest in a notch 194 in ceramic body 175. When the distal tip 190 is in the position of FIG. 2A, the tip 190 is distance D of at least 0.010" (see FIG. 2A) from the closest edge of window 195 of the metal body 185. As can be seen in FIGS. 2A-2C, the window edge 195 of metal body 185 is configured to have notch 200 that is larger than the notch 194 in ceramic body 175 to insure that the first and second electrodes, 120 and 122, are not in close proximity in the electrode position shown in FIG. 2A.

As can be seen in FIGS. 2B and 2C, the hook-shaped distal portion of electrode 120 can be extended axially and optionally rotationally to orient the distal tip 190 and terminal hook portion 196 for electrosurgical cutting of tissue as is known in the art using hook electrode tools. Thus, the electrode 120 is re-configurable to perform electrosurgical surface ablation treatments or electrosurgical cutting treatments. The electrode 120 can be a wire formed of tungsten, stainless steel or any other suitable material having a round, oval or polygonal cross section.

Figure 4:
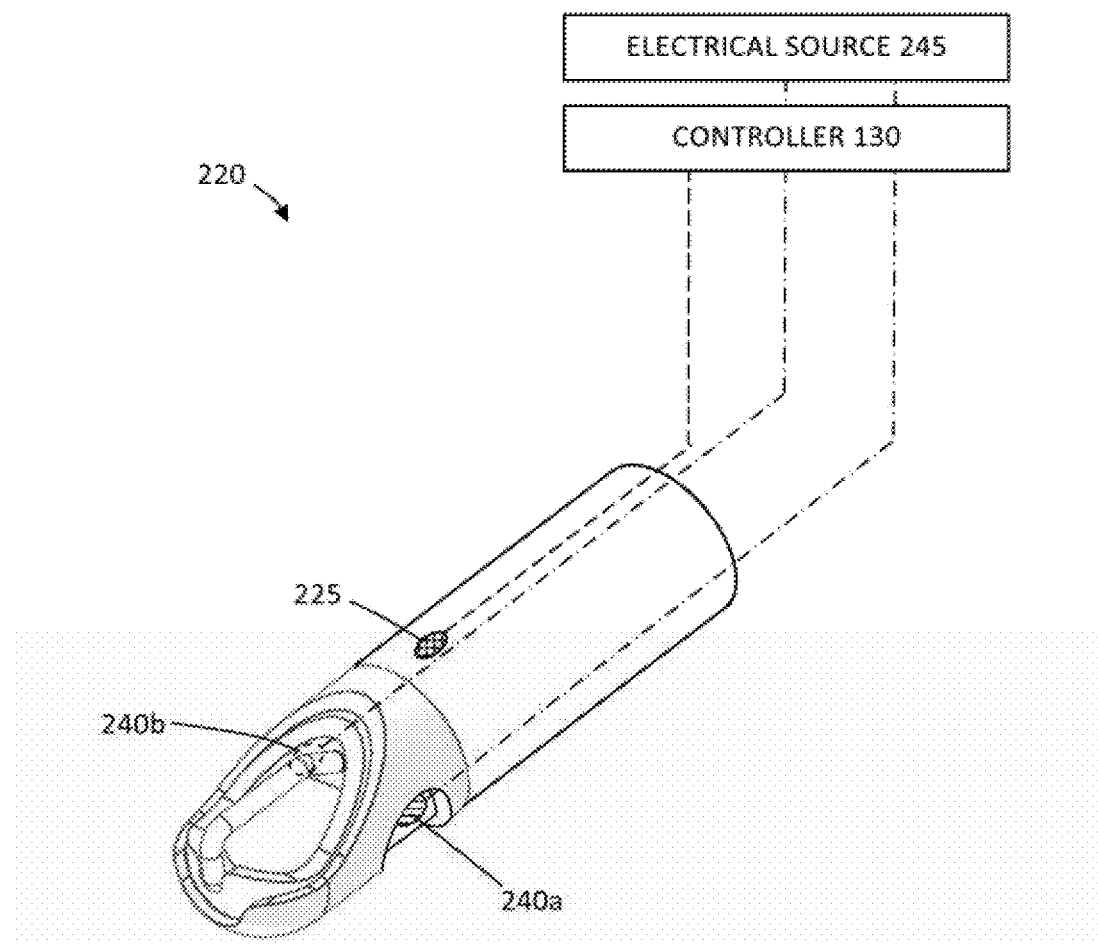
FIG. 4 is a perspective view of a working end of an electrosurgical device similar to that of FIG. 1 with temperature sensor for measuring the temperature of distention fluid in a joint and a controller that can signal an LED to illuminate as a high temperature alert to the physician.

Referring again to FIG. 3, in one variation, it can be seen that the bore 180 in sleeve 170 is lined with a thin-wall dielectric material 198 such a Teflon®, Nylon, PFA, FEP, polyethylene or the like which prevents the inner wall of sleeve 170 from functioning as an electrode. In another aspect of the invention, FIG. 4 illustrates a temperature sensing and signaling system that is carried within the working end 220 of a probe similar to that of FIGS. 1-3. Temperature sensing of distention fluid in an arthroscopic procedure is important as the fluid can be heated during any electrosurgical ablation procedure. If the distention fluid is at an elevated temperature for an excessive time period, tissue throughout the joint can be damaged. In FIG. 4, it can be seen a temperature sensor 225 is provided in a surface of the working end which can comprise any form of thermocouple, thermistor or other type of sensor. The sensor 225 is configured to send temperature signals to the controller 130 which can signal the operator of elevated temperature and/or terminate energy delivery from the RF source to the working end 220. In one variation shown in FIG. 5, the controller 130 can signal the physician of a high temperature signal from sensor 225 by illuminating LED lights 240a and 240b coupled to electrical source 245 on either side of the working end 220. In such an embodiment, the controller 130 may have algorithms for blinking the LEDs at increasing rates that increase with temperature of the distention fluid. Any combination of visual, aural and tactile signals may be used to alert the physician of elevated temperatures in the distention fluid. In another embodiment (not shown), the temperature sensor 225 can actuate at least one light source in the controller that is coupled to optical fibers to carry light to light emitters in the working end. In another variation, a plurality of different wavelength light sources in the controller can send different wavelengths to the emitter(s) in the working end to indicate different temperatures of the distention fluid.

Figure 5:
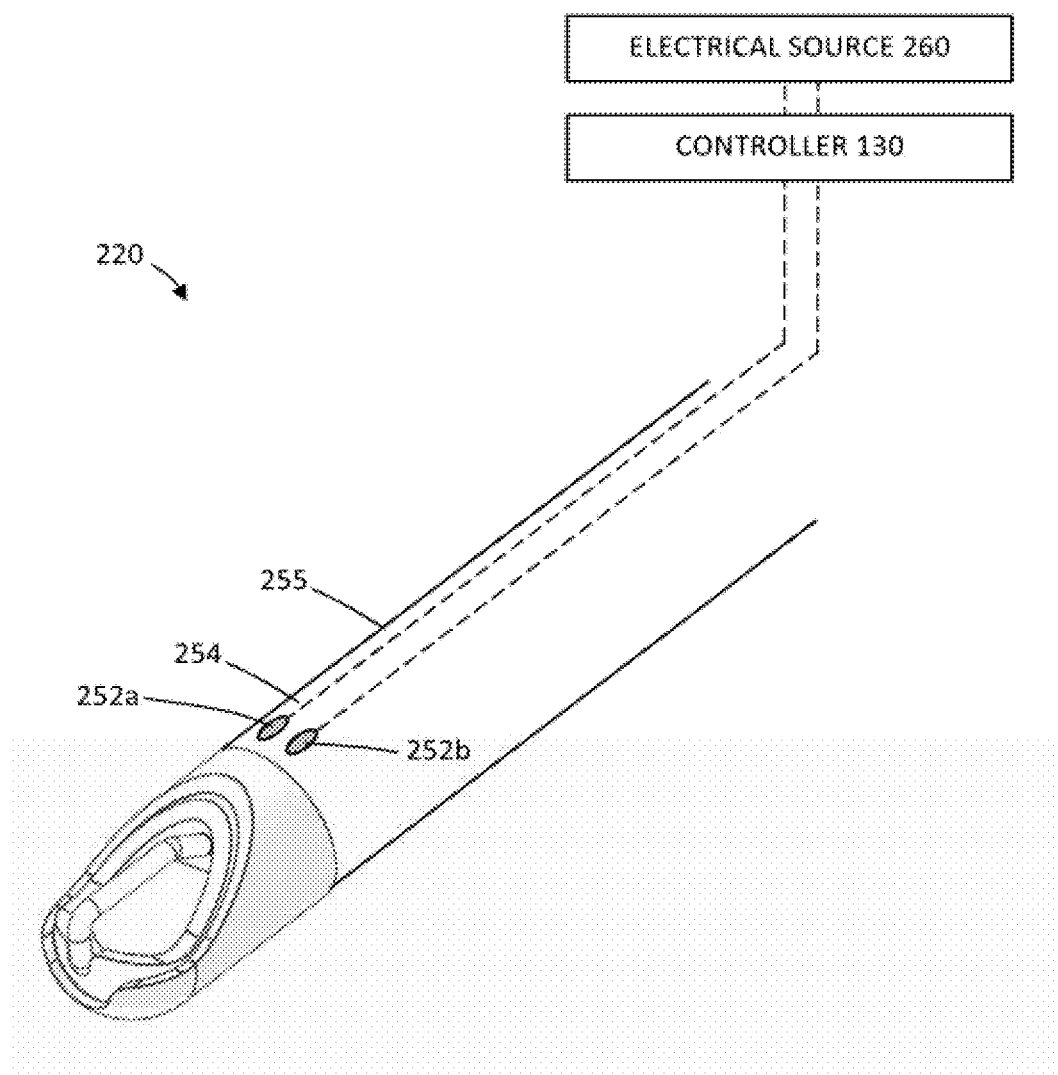
FIG. 5 is a perspective view of the working end of an electrosurgical device similar to that of FIG. 1 with a second electrode arrangement configured to measure impedance in distention fluid in a joint in order to determine the temperature of the fluid.

FIG. 5 illustrates another temperature sensing system that can be carried by the working end 220 as in FIG. 5. In FIG. 5, spaced apart first and second electrodes, 252a and 252b are provided in insulated surface 254 of the probe shaft 255. The electrodes 252a and 252b are coupled to an electrical source 255 and controller 130 which is configured to measure an electrical parameter of the distention fluid, for example impedance or capacitance of a saline distention fluid. The measured electrical parameter then can be compared to known values of saline at various temperatures in a look-up table to determine fluid temperature. The calculated temperature then can actuate any visual, aural or tactile signal to alert the physician of elevated temperatures in the saline.

Figure 6A:
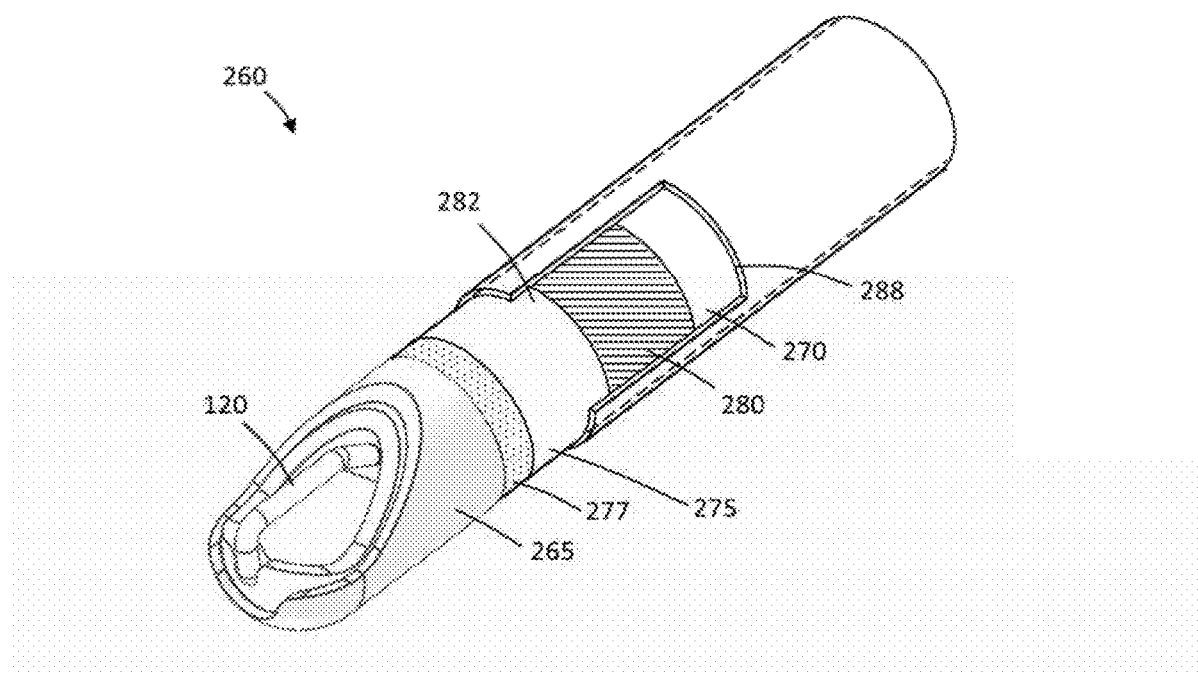
FIG. 6A is a cut-away perspective view of the working end of an ablation device similar to that of FIG. 1 with a PTCR (positive temperature coefficient of resistance) material in the return electrode assembly which can sense distention fluid temperature to de-activate the electrical path from the return electrode to the RF source.
Figure 6B:
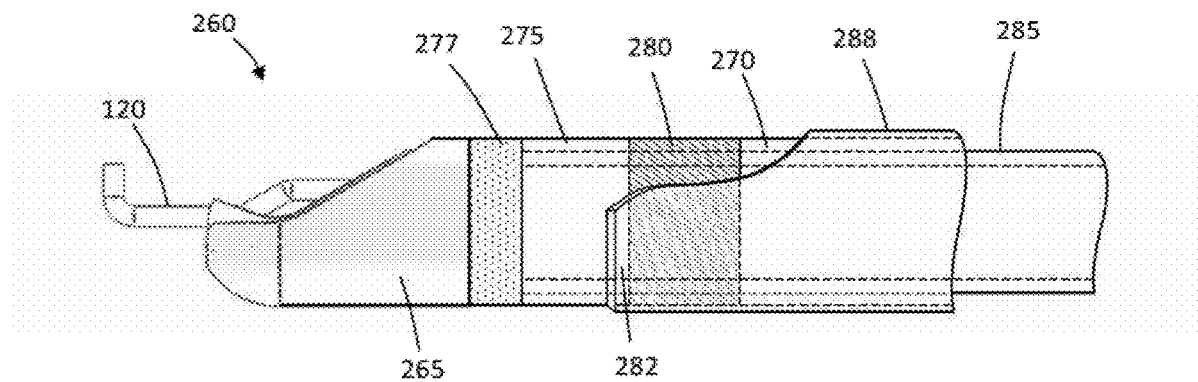
FIG. 6B is another cut-away view of the working end of FIG. 7A showing an inner sleeve that carries the working end assembly.

FIGS. 6A-6B illustrate another system embodiment that integrates a temperature sensing mechanism with the return electrode to control energy delivery to tissue. As can be seen in FIG. 6A, the working end 260 of a probe is similar to that of FIGS. 1-3. However, the distal metal housing 265 does not function as a return electrode. The metal housing 265 is not welded to elongated sleeve 270 which is electrically coupled to RF source 125 and controller 130. Rather, an independent return electrode sleeve 275 with a short length is positioned proximally from the distal metal housing 265. In one variation, an insulative ceramic collar 277 separates the distal metal housing 265 from the return electrode sleeve 275. The temperature-sensing component of the working end 260 comprises a polymer PTCR (positive temperature coefficient of resistance) sleeve 280 forms an intermediate electrical connector between the return electrode sleeve 275 and sleeve 270 which is electrically coupled to RF source 125 (see FIG. 1). The return electrode sleeve 275, the PTCR sleeve 280 and sleeve 270 can be mounted over insulated support sleeve 285 shown in FIG. 6B. The PTCR material of sleeve 280 allows conduction of RF current therethrough within a selected low temperature range, but can prevent current flow through the sleeve at a selected elevated temperature. As can be seen in FIGS. 6A-6B, the proximal end 282 of the return electrode 275, the PTCR sleeve 280 and the elongated sleeve 270 is covered with a thin-wall insulator 288 to thus prevent conductive saline contact with this portion of the probe. As can be understood in FIGS. 6A-6B, the thin-wall insulator 288 allows heat transfer from the distention fluid through the insulator 288 to the PTCR sleeve 280 which then can cause the PTCR sleeve to become non-conductive to terminate current flow from the return electrode 275 to the RF source 125. By this means, the PTCR mechanism can terminate RF energy delivery in response to elevated temperatures in the distention fluid. The PTCR material can be selected to have a any suitable switching temperature, for example any temperature between about 40° C. and 45° C. Suitable polymer PTCR materials can be fabricated by Bourns, Inc. 3910 Freedom Circle, Ste. 102, Santa Clara, Calif. 95954.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. An electrosurgical device, comprising:
an elongated shaft having a longitudinal axis with an interior channel extending along the axis to an opening in a distal surface of the shaft, said channel being configured to be coupled to a negative pressure source, wherein the distal surface is sloped relative to the longitudinal axis; and
an electrode with a hook-shaped distal tip, said electrode being moveable between a first position in which the distal tip is positioned within the opening in the distal surface and a second position in which the distal tip is spaced distally from a distal-most edge of the opening, wherein the electrode is mounted to axially translate between the first and second positions;

wherein a notch is formed in a periphery of the opening and the notch is configured to receive the hook-shaped distal tip of electrode when the electrode is in the first position.

2. The electrosurgical device of claim 1, wherein the electrode is mounted to axially translate and/or rotate about the axis between the first and second positions.

3. The electrosurgical device of claim 1, further comprising a valve in the interior channel for controlling fluid flow therethrough.

4. The electrosurgical device of claim 1, wherein an exterior of the shaft comprises a second electrode.

5. The electrosurgical device of claim 1, further comprising a rotator coupled to the electrode which causes the electrode to rotate as it is being axially translated.

6. The electrosurgical device of claim 1, further comprising a temperature sensor near a distal end of the shaft.

7. The electrosurgical device of claim 1, further comprising impedance sensing electrodes near a distal end of the shaft.

8. The electrosurgical device of claim 1, further comprising a temperature-response current limiting element in series with the electrode.

9. The electrosurgical device of claim 1, wherein the hook-shaped distal tip the electrode is configured to be turned so that a back of the hook-shaped distal tip extends laterally beyond the distal surface when the electrode is in the first position.

10. An electrosurgical device, comprising:
an electrically non-conductive elongated shaft extending along a longitudinal axis;
an electrically conductive distal housing coupled to a distal end of the elongated shaft and having an opening in a distal surface thereof; and
a moveable hook-shaped electrode having a conductive portion with a proximal end and a distal end, wherein the distal end of the conductive portion is disposed within the opening of the housing when the electrode is in a non-extended position and the distal end extends distally beyond the periphery when the electrode is in an extended position, wherein the electrode is mounted to axially translate between the first and second positions, wherein the opening is sloped relative to the longitudinal axis of the shaft and the hook portion the electrode is turned so that a back of the hook extends outwardly from the opening when the electrode is in the first position;
wherein a notch is formed in a periphery of the opening and the notch is configured to receive a distal tip of the hook-shaped of electrode when the electrode is in the first position and to receive a back portion of the electrode when the electrode is in its second position.

11. The electrosurgical device of claim 10, wherein the electrode is mounted to rotate about the axis between the first and second positions.

12. The electrosurgical device of claim 10, wherein the electrode is mounted to axially translate and/or rotate about the axis between the first and second positions.

13. The electrosurgical device of claim 10, further comprising a valve in the interior channel for controlling fluid flow therethrough.

14. The electrosurgical device of claim 10, wherein an exterior of the shaft comprises a second electrode.

15. The electrosurgical device of claim 10, further comprising a rotator coupled to the electrode which causes the electrode to rotate as it is being axially translated.

16. The electrosurgical device of claim 10, further comprising a temperature sensor near a distal end of the shaft.

17. The electrosurgical device of claim 10, further comprising impedance sensing electrodes near a distal end of the shaft.

18. The electrosurgical device of claim 10, further comprising a temperature-response current limiting element in series with the electrode.

19. An electrosurgical device, comprising:
an elongated member having a central axis with an interior channel and a passage extending axially in the member, said interior channel extending to an opening in a distal surface of the member and being configured to be coupled to a negative pressure source, wherein the distal surface is sloped relative to the central axis; and
an electrode having a shaft portion with a centerline and a distal spine portion with a length radially offset from said centerline, said distal spine portion extending across an axial length of the opening and said shaft portion rotatable within the passage to move the offset length of the spine portion in and out of the opening;
wherein a notch is formed in a periphery of the opening and the notch is configured to receive a distal tip of the electrode.

20. The electrosurgical device of claim 19, wherein the electrode shaft is mounted to axially translate in the passage.

21. The electrosurgical device of claim 19, further comprising a actuator for controlling fluid flow through the interior channel.

22. The electrosurgical device of claim 19, wherein an exterior of the shaft comprises a second electrode.

23. The electrosurgical device of claim 19, further comprising a rotator coupled to the electrode shaft which causes the electrode to rotate.

24. The electrosurgical device of claim 19, wherein the passage comprises a bore in the elongated member.

25. An electrosurgical device, comprising:
an elongated member having a central axis with an interior channel extending to an opening in a distal surface of the member and being configured to be coupled to a negative pressure source, wherein the distal surface is sloped relative to the central axis; and
an electrode having a shaft portion with a centerline and a distal spine portion with a length radially offset from said centerline, said shaft portion rotatable within the interior channel in the elongate member wherein the offset length of the spine portion can be moved laterally back and forth across the opening;
wherein a notch is formed in a periphery of the opening and the notch is configured to receive a distal tip of the electrode and to allow the offset length of the spine portion to be moved laterally back and forth across the opening.

* * * * *